United States Patent

Förster et al.

Patent Number: 5,097,038
Date of Patent: Mar. 17, 1992

[54] HERBICIDAL SUBSTITUTED THIADIAZOLYLOXYACETAMAIDES

[75] Inventors: Heinz Förster, Wuppertal; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 615,780

[22] Filed: Nov. 14, 1990

Related U.S. Application Data

[62] Division of Ser. No. 366,578, Jun. 15, 1989, Pat. No. 4,988,378.

[30] Foreign Application Priority Data

Jun. 27, 1988 [DE] Fed. Rep. of Germany ....... 3821599

[51] Int. Cl.[5] ............................................. C07D 285/13
[52] U.S. Cl. .................................................... 548/136
[58] Field of Search .......................................... 548/136

[56] References Cited

U.S. PATENT DOCUMENTS 4,708,731 11/1987 Förster .................................. 71/90

Primary Examiner—Robert Gerstl
Attorney, Agent, or Firm—Sprung Horn Kramer & Woods

[57] ABSTRACT

Herbicidal substituted thiadiazolyloxyacetamides of the formula

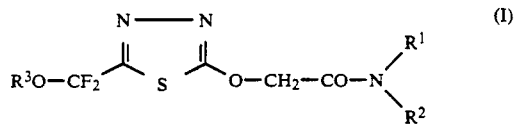

in which $R^1$ stands for hydrogen or for an optionally substituted radical from the group consisting of alkyl, alkenyl, alkinyl and aralkyl, $R^2$ stands for an optionally substituted radical from the group consisting of alkyl, alkenyl, alkinyl, cycloalkyl, cycloalkenyl, aralkyl, aryl, alkoxy, alkenyloxy and alkinyloxy, or $R^1$ and $R^2$ together with the nitrogen atom to which they are bonded form an optionally substituted, saturated or unsaturated heterocycle which can contain further hetero atoms and to which a benzo group can be fused, and $R^3$ stands for an optionally substituted alkyl radical.

Intermediates of the formulas

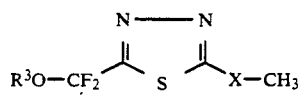

and

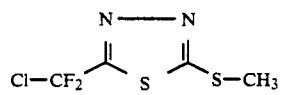

in which
$R^3$ stands for optionally substituted alkyl, and
X stands for S or $SO_2$,
are also new.

1 Claim, No Drawings

HERBICIDAL SUBSTITUTED THIADIAZOLYLOXYACETAMAIDES

This is a division of application Ser. No. 366,578, filed June 15, 1989, now U.S. Pat. No. 4,981,378.

The invention relates to novel substituted thiadiazolyloxyacetamides, a process and novel intermediates for their preparation and their use as herbicides.

It has already been disclosed that certain heteroaryloxyacetamides, such as, for example, N-methyl-2-(benzothiazol-2-yl-oxy)-acetanilide, show herbicidal properties (cf. U.S. Pat. No. 4,509,971). However, the herbicidal activity of the previously known compounds is not always completely satisfactory.

Novel substituted thiadiazolyloxyacetamides of the general formula (I)

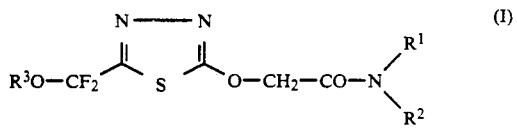

in which
- $R^1$ stands for hydrogen or for an optionally substituted radical from the series comprising alkyl, alkenyl, alkinyl or aralkyl,
- $R^2$ stands for an optionally substituted radical from the series comprising alkyl, alkenyl, alkinyl, cycloalkyl, cycloalkenyl, aralkyl, aryl, alkoxy, alkenyloxy or alkinyloxy, or
- $R^1$ and $R^2$ together with the nitrogen atom to which they are bonded form an optionally substituted, saturated or unsaturated heterocycle which can contain further hetero atoms and to which a benzo group can be fused, and
- $R^3$ stands for an optionally substituted alkyl radical, have now been found.

Furthermore, it has been found that the novel substituted thiadiazolyloxyacetamides of the general formula (I) are obtained when methylsulphonylthiadiazoles of the general formula (II)

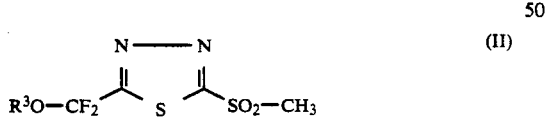

in which
$R^3$ has the abovementioned meaning, are reacted with hydroxyacetamides of the general formula (III)

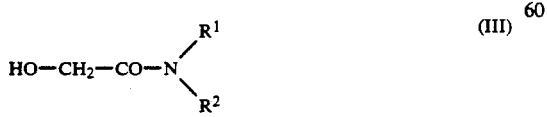

in which
$R^1$ and $R^2$ have the abovementioned meanings, if appropriate in the presence of a diluent, if appropriate in the presence of an acid-binding agent and if appropriate in the presence of a catalyst.

Finally, it has been found that the novel substituted thiadiazolyloxyacetamides of the general formula (I) possess interesting herbicidal properties.

Surprisingly, the novel substituted thiadiazolyloxyacetamides of the general formula (I) show a considerably more powerful herbicidal action against common weeds which are difficult to control than the abovementioned compound while having good tolerance towards important crop plants.

The invention preferably relates to compounds of the formula (I) in which
- $R^1$ stands for hydrogen, $C_1$-$C_8$-alkyl which is optionally substituted by fluorine, chlorine, cyano or $C_1$-$C_4$-alkoxy, for $C_2$-$C_8$-alkenyl which is optionally substituted by fluorine and/or chlorine, for $C_2$-$C_8$-alkinyl or for benzyl,
- $R^2$ stands for $C_1$-$C_8$-alkyl which is optionally substituted by fluorine, chlorine, cyano or $C_1$-$C_4$-alkoxy, for $C_2$-$C_8$-alkenyl which is optionally substituted by fluorine and/or chlorine, for $C_2$-$C_8$-alkinyl, for $C_3$-$C_6$-cycloalkyl which is optionally substituted by chlorine and/or $C_1$-$C_3$-alkyl, for $C_5$- or $C_6$-cycloalkenyl, for benzyl which is optionally substituted by fluorine, chlorine and/or $C_1$-$C_4$-alkyl, for phenyl which is optionally substituted by fluorine, chlorine, bromine, iodine, cyano, nitro, $C_1$-$C_4$-alkyl, trifluoromethyl, $C_1$-$C_4$-alkoxy and/or $C_1$-$C_4$-alkylthio, for $C_1$-$C_8$-alkoxy which is optionally substituted by $C_1$-$C_4$-alkoxy, or for $C_3$-$C_4$-alkenyloxy, or
- $R^1$ and $R^2$ together with the nitrogen atom to which they are bonded form a saturated or unsaturated, five- to seven-membered nitrogen heterocycle which is optionally monosubstituted to trisubstituted by $C_1$-$C_3$-alkyl and which is optionally benzo-fused, and
- $R^3$ stands for $C_1$-$C_6$-alkyl which is optionally substituted by halogen, $C_1$-$C_4$-alkoxy, $C_1$-$C_4$-alkylsulphonyl, phenyl, phenoxy or phenyl-$C_1$-$C_4$-alkoxy, the phenyl component being optionally substituted by halogen, $C_1$-$C_4$-alkyl, trifluoromethyl and/or $C_1$-$C_4$-alkoxy.

The invention particularly relates to compounds of the formula (I) in which
- $R^1$ stands for $C_1$-$C_4$-alkyl, allyl or propargyl,
- $R^2$ stands for $C_1$-$C_6$-alkyl, $C_1$-$C_2$-alkoxy-$C_1$-$C_2$-alkyl, allyl, propargyl, cyclopentyl, cyclohexyl, cyclohexenyl, benzyl, phenyl (which is optionally substituted by fluorine, chlorine, bromine, cyano, nitro, methyl, ethyl, trifluoromethyl, methoxy or ethoxy), $C_1$-$C_6$-alkoxy or $C_1$-$C_2$-alkoxy-$C_1$-$C_2$-alkoxy, or
- $R^1$ and $R^2$ together with the nitrogen atom to which they are bonded stand for piperidinyl which is optionally monosubstituted to trisubstituted by methyl and/or ethyl, for pyrrolidinyl which is optionally monosubstituted or disubstituted by methyl and/or ethyl, for perhydroazepinyl or for 1,2,3,4-tetrahydroquinolinyl, and
- $R^3$ stands for methyl, ethyl, propyl, isopropyl, butyl, isobutyl, sec-butyl, tert-butyl, trifluoroethyl, trichloroethyl, methoxyethyl, ethoxyethyl, methylsulphonylethyl, ethylsulphonylethyl, benzyl, chlorobenzyl, phenylethyl or benzyloxyethyl.

Examples of the compounds of the formula (I) are listed in Table 1 below.

TABLE 1

Examples of the compounds of the formula (I)

$$R^3O-CF_2-\underset{S}{\overset{N=N}{\complement}}-O-CH_2-CO-N\underset{R^2}{\overset{R^1}{<}} \qquad (I)$$

| $R^3$ | $R^1$ | $R^2$ | or $-N\underset{R^2}{\overset{R^1}{<}}$ |
|---|---|---|---|
| $CH_3$ | $CH_3$ | $CH_3$ | |
| $CH_3$ | $C_2H_5$ | $C_2H_5$ | |
| $CH_3$ | $C_3H_7$ | $C_3H_7$ | |
| $CH_3$ | $C_4H_9$ | $C_4H_9$ | |
| $CH_3$ | $CH_3$ | $C_4H_9$ | |
| $CH_3$ | $CH_3$ | $CH(CH_3)C_2H_5$ | |
| $CH_3$ | $CH_2CH=CH_2$ | $CH_2CH=CH_2$ | |
| $CH_3$ | $CH_2C\equiv CH$ | $CH_2C\equiv CH$ | |
| $CH_3$ | $CH(CH_3)C_2H_5$ | $OCH_3$ | |
| $CH_3$ | $CH(CH_3)_2$ | $OCH(CH_3)_2$ | |
| $CH_3$ | $CH(CH_3)_2$ | $OCH_2CH_2OC_2H_5$ | |
| $CH_3$ | $CH_3$ | $C_5H_{11}$ | |
| $CH_3$ | $CH_3$ | $C_6H_{13}$ | |
| $CH_3$ | $CH_3$ | cyclopentyl | |
| $CH_3$ | $CH_3$ | cyclohexyl | |
| $CH_3$ | $CH_3$ | phenyl | |
| $CH_3$ | $CH_3$ | cyclohex-1-enyl | |
| $CH_3$ | $CH_3$ | 2-methylphenyl | |
| $CH_3$ | $CH_3$ | 3-methylphenyl | |
| $CH_3$ | $CH_3$ | 4-methylphenyl | |

TABLE 1-continued

Examples of the compounds of the formula (I)

$$R^3O-CF_2-\underset{\substack{\| \\ N-N}}{C}-S-\underset{\substack{\| \\ }}{C}-O-CH_2-CO-N\underset{R^2}{\overset{R^1}{\diagdown}} \quad (I)$$

| $R^3$ | $R^1$ | $R^2$ | or $-N\overset{R^1}{\underset{R^2}{\diagdown}}$ |
|---|---|---|---|
| CH$_3$ | CH$_3$ | 2-chlorophenyl | |
| CH$_3$ | CH$_3$ | 3-chlorophenyl | |
| CH$_3$ | CH$_3$ | 4-chlorophenyl | |
| CH$_3$ | CH$_3$ | —CH$_2$—phenyl | |
| CH$_3$ | CH$_3$ | 2,3-dimethylphenyl | |
| CH$_3$ | CH$_3$ | 3-trifluoromethylphenyl | |
| CH$_3$ | CH$_3$ | 4-methoxyphenyl | |
| CH$_3$ | | | hexamethyleneimino |
| CH$_3$ | | | 2-methylpiperidino |
| CH$_3$ | | | 4-methylpiperidino |

TABLE 1-continued
Examples of the compounds of the formula (I)
$$R^3O-CF_2-\underset{S}{\overset{N-N}{\underset{\|}{C}}}\overset{\|}{C}-O-CH_2-CO-N\overset{R^1}{\underset{R^2}{}}$$  (I)
| R³ | R¹ | R² | or $-N\overset{R^1}{\underset{R^2}{}}$ |
|---|---|---|---|
| CH₃ | | | 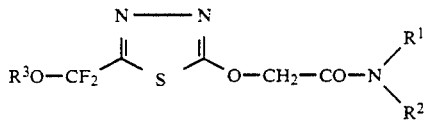 |
| CH₃ | | | 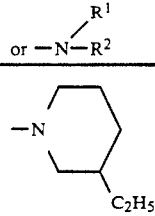 |
| CH₃ | | | 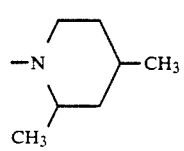 |
| CH₃ | C₂H₅ | 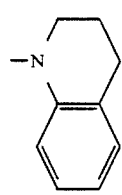 | |
| CH₃ | CH(CH₃)₂ | 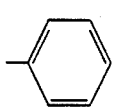 | |
| CH₃ | CH(CH₃)₂ | 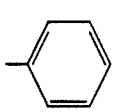 | |
| CH₃ | CH(CH₃)₂ | 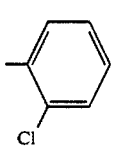 | |
| CH₃ | CH(CH₃)₂ | 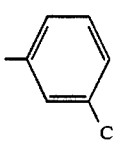 | |
| CH₃ | CH(CH₃)₂ | 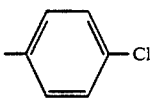 | |
| CH₃ | CH(CH₃)₂ | 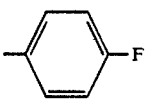 | |

TABLE 1-continued

Examples of the compounds of the formula (I)

$$R^3O-CF_2-C(=N-N=)-S-C(=...)-O-CH_2-CO-N(R^1)(R^2)$$ (I)

| R³ | R¹ | R² | or —N(R¹)(R²) |
|---|---|---|---|
| CH₃ | CH(CH₃)₂ | | 3-CF₃-C₆H₄– |
| CH₃ | C₃H₇ | | C₆H₅– |
| C₂H₅ | CH₃ | C₄H₉ | |
| C₂H₅ | C₂H₅ | C₂H₅ | |
| C₂H₅ | CH(CH₃)₂ | CH₂CH₂OC₂H₅ | |
| C₂H₅ | CH₃ | | C₆H₅– |
| C₂H₅ | CH(CH₃)₂ | | C₆H₅– |
| C₃H₇ | CH₃ | | C₆H₅– |
| C₃H₇ | CH(CH₃)₂ | | C₆H₅– |
| C₃H₇ | C₃H₇ | C₃H₇ | |
| CH(CH₃)₂ | C₂H₅ | C₂H₅ | |
| CH(CH₃)₂ | CH₃ | | C₆H₅– |
| CH(CH₃)₂ | CH(CH₃)₂ | | C₆H₅– |
| C₄H₉ | CH₃ | | C₆H₅– |
| CH₂CH₂OCH₃ | CH₃ | | C₆H₅– |

TABLE 1-continued

Examples of the compounds of the formula (I)

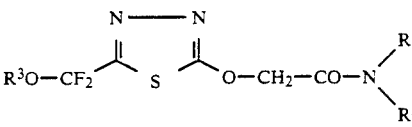

| R³ | R¹ | R² | or $-N\begin{smallmatrix}R^1\\R^2\end{smallmatrix}$ |
|---|---|---|---|
| CH₂CH₂OCH₃ | C₂H₅ | C₂H₅ | |
| CH₂CH₂OC₂H₅ | CH₃ | | phenyl |
| CH₂—phenyl | CH₃ | | phenyl |
| CH₂CH₂OCH₂—phenyl | CH₃ | | phenyl |
| CH₂CF₃ | CH₃ | | phenyl |

If, for example, 2-methylsulphonyl-5-methoxy-difluoromethyl-1,3,4-thiadiazole and hydroxyacetopiperidide are used as starting substances, the course of the reaction in the process according to the invention can be represented by the following equation:

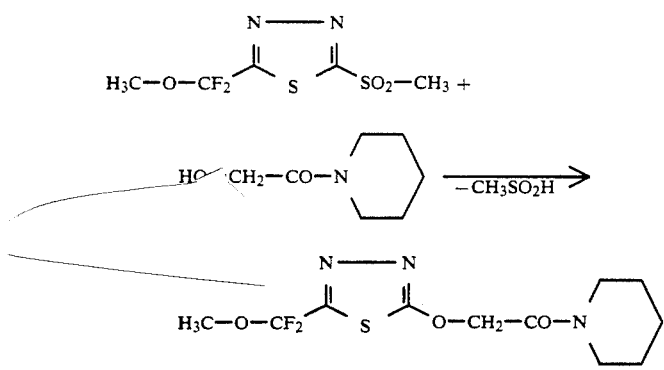

Formula (II) provides a general definition of the methylsulphonylthiadiazoles to be used as starting substances in the process according to the invention for the preparation of compounds of the formula (I).

In formula (II), R³ preferably, or in particular, has the meaning which has already been mentioned above in connection with the description of the compounds of the formula (I) according to the invention as being preferred, or particularly preferred, respectively, for R³.

Examples of the starting substances of the formula (II) which may be mentioned are: 5-methoxy-difluoromethyl-, 5-ethoxydifluoromethyl-, 5-propoxydifluoromethyl-, 5-isopropoxydifluoromethyl-, 5-butoxydifluoromethyl-, 5-isobutoxydifluoromethyl-, 5-sec-butoxydifluoromethyl-, 5-tert-butoxydifluoromethyl-, 5-(2,2,2-trifluoroethoxy)-difluoromethyl-, 5-(2,2,2-trichloroethoxy)-difluoromethyl-, 5-(2-methoxyethoxy)-difluoromethyl-, 5-(2-ethoxyethoxy)-difluoromethyl-, 5-(2-methylsulphonylethoxy)-difluoromethyl-, 5-(2-ethylsulphonylethoxy)-difluoromethyl-, 5-benzyloxydifluoromethyl-, 5-(1-phenylethoxy)-difluoromethyl-, 5-(2-phenylethoxy)-difluoromethyl-, 5-(2-chloro-benzyloxy)-difluoromethyl-, 5-(3-chloro-benzyloxy)-difluoromethyl-, 5-(4-chloro-benzyloxy)-difluoromethyl- and 5-(2-benzyloxy-ethoxy)-difluoromethyl-2-methylsulphonyl-1,3,4-thiadiazole.

The starting substances of the formula (II) were hitherto unknown from the literature and also form the subjectmatter of the present invention.

The novel compounds of the formula (II) are obtained when methylthio-thiadiazoles of the general formula (IV)

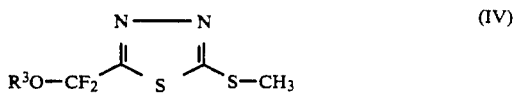

in which
R³ has the abovementioned meaning,
are reacted with an oxidizing agent, such as, for example, hydrogen peroxide, if appropriate in the presence of a catalyst, such as, for example, sodium tungstate, and if appropriate in the presence of diluents, such as, for example, water, formic acid and/or acetic acid, at temperatures between 0° C. and 100° C.

Formula (IV) provides a general definition of the methylthiothiadiazoles required as intermediates. In formula (IV), R³ preferably, or in particular, has the meaning which has already been mentioned above in connection with the description of the compounds of the formula (I) according to the invention as being preferred, or particularly preferred, respectively, for R³.

Examples of the intermediates of the formula (IV) which may be mentioned are: 5-methoxy-difluoromethyl-, 5-ethoxydifluoromethyl-, 5-propoxydifluoromethyl-, 5-isopropoxydifluoromethyl-, 5-butoxydifluoromethyl-, 5-isobutoxydifluoromethyl-, 5-sec-butoxydifluoromethyl-, 5-tert-butoxydifluoromethyl-, 5-(2,2,2-trifluoroethoxy)-difluoromethyl-, 5-(2,2,2-trichloroethoxy)-difluoromethyl-, 5-(2-methoxyethoxy)-difluoromethyl-, 5-(2-ethoxyethoxy)-difluoromethyl-, 5-(2-methylsulphonylethoxy)-difluoromethyl-, 5-(2-ethylsulphonylethoxy)-difluoromethyl-, 5-benzyloxydifluoromethyl-, 5-(1-phenylethoxy)-difluoromethyl-, 5-(2-phenylethoxy)-difluoromethyl-, 5-(2-chloro-benzyloxy)-difluoromethyl-, 5-(3-chloro-benzyloxy)-difluoromethyl-, 5-(4-chloro-benzyloxy)-difluoromethyl- and 5-(2-benzyloxy-ethoxy)-difluoromethyl-2-methylthio-1,3,4-thiadiazole.

The intermediates of the formula (IV) were hitherto unknown from the literature and also form the subject-matter of the present invention.

The novel compounds of the formula (IV) are obtained when 5-chlorodifluoromethyl-2-methylthio-1,3,4-thiadiazole of the formula (V)

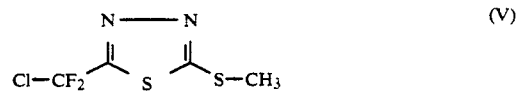

is reacted with hydroxy compounds of the general formula (VI)

R³—OH         (VI)

in which

R³ has the abovementioned meaning, or with sodium or potassium salts thereof, if appropriate in the presence of diluents, such as, for example, acetone, acetonitrile or toluene, at temperatures between 0° C. and 50° C.

5-Chlorodifluoromethyl-2-methylthio-1,3,4-thiadiazole, of the formula (V), was hitherto unknown from the literature and also forms the subject-matter of the present invention.

The novel compound of the formula (V) is obtained when chlorodifluoroacetic acid is reacted with methyl dithiocarbazate in the presence of phosphorus oxychloride and if appropriate in the presence of an acid acceptor, such as, for example, potassium carbonate, and if appropriate in the presence of a diluent, such as, for example, toluene, at temperatures between 0° C. and 100° C.

Formula (III) provides a general definition of the hydroxyacetamides also to be used as starting substances. In formula (III), R¹ and R² preferably, or in particular, have those meanings which have already been mentioned above in connection with the description of the compounds according to the invention of the formula (I) as being preferred, or particularly preferred, respectively, for R¹ or R².

Examples of the starting substances of the formula (III) are listed in Table 2 below.

TABLE 2

Examples of the starting substances of the formula (III)

| R¹ | R² | R¹ | R² |
|---|---|---|---|
| CH₃ | OCH(CH₃)₂ | CH₃ | OCH₂CH₂OC₂H₅ |
| CH₃ | CH(CH₃)₂ | CH₃ | CH₂CH(CH₃)₂ |
| CH₃ | CH—CH₂CH₂ \| CH₃ | C₂H₅ | OC₂H₅ |
| C₂H₅ | OCH₂CH₂OC₂H₅ | C₂H₅ | OCH₂CH(CH₃)₂ |
| CH₃ | ⟨phenyl⟩ | CH₃ | ⟨phenyl⟩—F |
| CH₃ | ⟨phenyl⟩—Cl | CH₃ | ⟨phenyl⟩—CH₃ |
| CH₃ | ⟨phenyl⟩—OCH₃ | CH₃ | ⟨phenyl⟩—SCH₃ |

TABLE 2-continued

Examples of the starting substances of the formula (III)

$$HO-CH_2-CO-N\begin{matrix}R^1\\R^2\end{matrix} \quad (III)$$

| $R^1$ | $R^2$ | $R^1$ | $R^2$ |
|---|---|---|---|
| CH₃ | 4-CF₃-C₆H₄ | CH₃ | 3-CF₃-C₆H₄ |
| CH₃ | 2-F-C₆H₄ | CH₃ | 3,4-Cl₂-C₆H₃ |
| CH₃ | 2-CH₃-4-NO₂-C₆H₃ | C₂H₅ | C₆H₅ |
| CH₃ | 2,6-Cl₂-C₆H₃ | CH₃ | 3,4-Cl₂-C₆H₃ |
| CH₃ | 2,3-(CH₃)₂-C₆H₃ | CH₃ | 2-CH₃-C₆H₄ |
| CH₃ | 3-Cl-C₆H₄ | CH₃ | 3-F-C₆H₄ |
| CH₃ | cyclohexenyl | CH₃ | CH₃ |
| CH(CH₃)₂ | C₆H₅ | C₂H₅ | 4-F-C₆H₄ |
| C₂H₅ | 4-Cl-C₆H₄ | C₂H₅ | 3-Cl-C₆H₄ |
| CH(CH₃)₂ | 4-F-C₆H₄ | CH(CH₃)₂ | 4-Cl-C₆H₄ |

TABLE 2-continued

Examples of the starting substances of the formula (III)

$$HO-CH_2-CO-N\begin{matrix}R^1\\R^2\end{matrix}\qquad(III)$$

| $R^1$ | $R^2$ | $R^1$ | $R^2$ |
|---|---|---|---|
| CH(CH$_3$)$_2$ | 4-CH$_3$-C$_6$H$_4$ | CH(CH$_3$)$_2$ | 3-Cl-C$_6$H$_4$ |
| CH(CH$_3$)$_2$ | 3,4-Cl$_2$-C$_6$H$_3$ | CH(CH$_3$)$_2$ | 2-Cl-C$_6$H$_4$ |
| C$_2$H$_5$ | C$_2$H$_5$ | C$_3$H$_7$ | C$_3$H$_7$ |
| CH(CH$_3$)$_2$ | CH(CH$_3$)$_2$ | CH(CH$_3$)$_2$ | OCH$_3$ |
| CH(CH$_3$)$_2$ | OCH$_2$CH$_2$OC$_2$H$_5$ | CH(CH$_3$)$_2$ | OC$_2$H$_5$ |
| CH(CH$_3$)$_2$ | OC$_3$H$_7$ | CH$_3$ | OCH$_2$CH(CH$_3$)$_2$ |
| CH$_3$ | CH$_2$OCH$_3$ | C$_4$H$_9$ | C$_4$H$_9$ |
| C$_2$H$_5$ | OCH$_3$ | CH$_3$ | CH$_2$CF$_3$ |
| CH$_2$CH=CH$_2$ | CH$_2$CH=CH$_2$ | CH$_2$C≡CH | CH$_2$C≡CH |
| CH$_3$ | CH$_2$C≡CH | CHCH$_2$CH$_3$ $\vert$ CH$_3$ | OCH$_3$ |
| CHCH$_2$CH$_3$ $\vert$ CH$_3$ | OCH$_3$ | CH$_3$ | CH$_2$-C$_6$H$_5$ |
| C$_2$H$_5$ | CH$_2$-C$_6$H$_5$ | CH(CH$_3$)$_2$ | CH$_2$-C$_6$H$_5$ |
| C$_2$H$_5$ | CH$_2$C≡CH | CH(CH$_3$)$_2$ | CH$_2$C≡CH |
| CH(CH$_3$)$_2$ | OCH(CH$_3$)$_2$ | | |

| $-N\begin{matrix}R^1\\R^2\end{matrix}$ | $-N\begin{matrix}R^1\\R^2\end{matrix}$ |
|---|---|
| pyrrolidin-1-yl | piperidin-1-yl |
| 2-methylpiperidin-1-yl | 4-methylpiperidin-1-yl |
| 3-methylpiperidin-1-yl | hexahydroazepin-1-yl |

TABLE 2-continued

Examples of the starting substances of the formula (III)

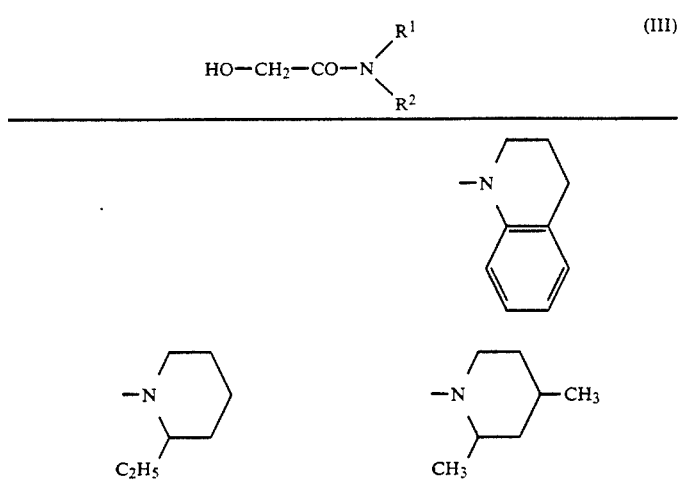

The hydroxyacetamides of the formula (III) are known and/or can be prepared by processes known per se (cf. U.S. Pat. Nos. 4,509,971 and 4,645,525; furthermore U.S. Pat. No. 4,334,073, DE-A 3,038,598, DE-A 3,038,636 and EP-A 37,526).

The process according to the invention for the preparation of the novel substituted thiadiazolyloxyacetamides of the formula (I) is preferably carried out using diluents. These preferably include hydrocarbons, such as, for example, toluene, xylene or cyclohexane, halogenohydrocarbons, such as, for example, methylene chloride, ethylene chloride, chloroform or chlorobenzene, ethers, such as, for example, diethyl ether, dipropyl ether, diisopropyl ether, dibutyl ether, diisobutyl ether, glycol dimethyl ether, tetrahydrofuran and dioxane, alcohols, such as, for example, methanol, ethanol, propanol, isopropanol or butanol, ketones, such as, for example, acetone, methyl ethyl ketone, methyl isopropyl ketone and methyl isobutyl ketone, esters, such as, for example, methyl acetate and ethyl acetate, amides, such as, for example, dimethylformamide, dimethylacetamide and N-methyl-pyrrolidone, nitriles, such as, for example, acetonitrile and propionitrile, sulphoxides, such as, for example, dimethyl sulphoxide, and also water or aqueous salt solutions.

Salts which can preferably be used are chlorides or sulphates of alkali metals or alkaline earth metals, such as, for example, sodium chloride, potassium chloride or calcium chloride. Sodium chloride is particularly preferred.

The process according to the invention is advantageously carried out using acid-binding agents. Acid-binding agents which are preferably used are strongly basic alkali metal compounds and alkaline earth metal compounds, for example oxides, such as, for example, sodium oxide, potassium oxide, magnesium oxide and calcium oxide, hydroxides, such as, for example, sodium hydroxide, potassium hydroxide, magnesium hydroxide and calcium hydroxide and/or carbonates, such as, for example, sodium carbonate, potassium carbonate, magnesium carbonate and calcium carbonate.

The addition of 0.01 to 10% by weight (based on glycolamide employed, of the formula (III)) of a phase transfer catalyst may prove advantageous in some cases. Examples of such catalysts which may be mentioned are: tetrabutylammonium chloride, tetrabutylammonium bromide, tributyl-methylphosphonium bromide, trimethyl-$C_{13}/C_{15}$-alkyl-ammonium chloride, dibenzyl-dimethyl-ammonium methylsulphate, dimethyl-$C_{12}/C_{14}$-alkyl-benzylammonium chloride, tetrabutylammonium hydroxide, 18-crown-6, triethylbenzylammonium chloride, trimethylbenzylammonium chloride, tetraethylammonium bromide.

In the process according to the invention, the reaction temperatures can be varied within a relatively wide range. In general, the process is carried out at temperatures between −50° C. and +110° C., preferably at temperatures between −20° C. and +100° C.

In general, the process according to the invention is carried out under atmospheric pressure, but it can can also be carried out at increased or reduced pressure, e.g. between 0.1 and 10 bar.

For carrying out the process according to the invention, 0.5 to 5 moles, preferably 0.8 to 1.5 moles, of hydroxyacetamide of the formula (III) are generally employed per mole of methylsulphonylthiadiazole of the formula (II). The reactants can be combined in any desired sequence. The reaction mixture is in each case stirred until the reaction is complete, and the work-up is carried out by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively combating monocotyledon weeds in monocotyledon and dicotyledon crops, especially using the pre-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans; furthermore also N-(methoxymethyl)-2,6-diethyl-chloroacetanilide (ALACHLOR); 2-chloro-4-ethylamino-6-isopropylamino-1,3,5-triazine (ATRAZIN); methyl 2-[[[[(4,6-dimethoxypyrimidin-2-yl)-amino]-carbonyl]-amino]-sulphonyl]-methyl]-benzoate (BENSULFURON); N-(butoxymethyl)-2-chloro-N-(2,6-diethylphenyl)-acetamide (BUTACHLOR); 5-amino-4-chloro-2-phenyl-2,3-dihydro-3-oxy-pyridazine (CHLORIDAZON); ethyl 2-{[(4-chloro-6-methoxy-2-pyrimidinyl)-aminocarbonyl]-aminosulphonyl}-benzoate (CHLORIMURON); 2-chloro-N-{[(4-methoxy-6-methyl-1,3,5-triazin-2-yl)-amino]-carbonyl}-benzenesulphonamide (CHLORSULFURON); exo-1-methyl-4-(1-methylethyl)-2-(2-methylphenyl-methoxy)-7-oxabicyclo-(2,2,1)-heptane (CINMETHYLIN); 2-chloro-4-ethylamino-6-(3-cyanopropylamino)-1,3,5-triazine (CYANAZINE); N,S-diethyl N-cyclohexyl-thiolcarbamate (CYCLOATE); 2-[(2-chlorophenyl)-methyl]-4,4-dimethylisoxazolidin-3-one (DIMETHAZONE); S-ethyl N,N-di-n-propyl-thiocarbamate (EPTAME); 4-amino-6-t-butyl-3-ethylthio-1,2,4-triazin-5(4H)-one (ETHIOZIN); N,N-dimethyl-N'-(3-trifluoromethylphenyl)-urea (FLUOMETURON); 1-methyl-3-phenyl-5-(3-trifluoromethylphenyl)-4-pyridone (FLURIDONE); methyl 2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); N-methyl-2-(1,3-benzothiazol-2-yloxy)-acetanilide (MEFENACET); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); S-ethyl N,N-hexamethylenethiolcarbamate (MOLINATE); 4-(di-n-propylamino)-3,5-dinitrobenzenesulphonamide (ORYZALIN); N-(1-ethylpropyl)-3,4-dimethyl-2,6-dinitroaniline (PENDIMETHALIN); α-chloro-2',6'-diethyl-N-(2-propoxyethyl)-acetanilide (PRETILACHLOR); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-2,3,3-trichloroallyl N,N-diisopropylthiolcarbamate (TRI-ALLATE) and 2,6-dinitro-4-trifluoromethyl-N,N-dipropylaniline (TRIFLURALIN). Suprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

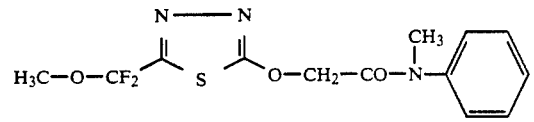

A solution of 0.88 g (0.022 mol) of sodium hydroxide in 4 ml of water is added dropwise to a stirred mixture of 4.0 g (0.0189 mol) of 5-methoxydifluoromethyl-2-methylsulphonyl-1,3,4-thiadiazole, 3.1 g (0.0189 mol) of N-methyl-hydroxyacetanilide and 40 ml of acetone, which had been cooled to $-20°$ C. The reaction mixture is stirred for 12 hours with cooling using ice/common salt. The mixture is then acidified using acetic acid and concentrated under a waterpump vacuum. The residue is shaken with water/toluene, and the organic phase is washed with water, dried using sodium sulphate and filtered. The solvent is carefully removed from the filtrate by distillation under a waterpump vacuum.

5.8 g (93% of theory) of N-methyl-(5-methoxy-difluoromethyl-1,3,4-thiadiazol-2-yl)-oxyacetanilide are obtained as an oily residue of refractive index $n^{20} = 1.5350$.

The compounds of the formula (I) listed in Table 3 below can also be prepared analogously to Example 1 and following the general instructions of the preparation process according to the invention:

TABLE 3

Preparation Examples of the compounds of the formula (I)

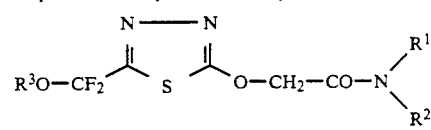

| Example No. | $R^3$ | $R^1$ $R^2$ or $-N\!\!<^{R^1}_{R^2}$ | | Physical data (m.p. = melting point) |
|---|---|---|---|---|
| 2 | $CH_3$ | $CH(CH_3)_2$ | (2-chlorophenyl) | m.p.: 51° C. |
| 3 | $CH_3$ | $CH(CH_3)_2$ | (phenyl) | m.p.: 83° C. |
| 4 | $CH_3$ | $CH(CH_3)_2$ | $OCH_2CH_2OC_2H_5$ | $n_D^{20}$: 1.4640 |

TABLE 3-continued

Preparation Examples of the compounds of the formula (I)

$$R^3O-CF_2-\underset{\underset{S}{||}}{C}\underset{N\!=\!\!=\!\!=\!\!N}{\overset{}{\diagdown}}\underset{}{C}-O-CH_2-CO-N\diagup\!\!\!\!\diagdown\underset{R^2}{\overset{R^1}{}} \quad (I)$$

| Example No. | $R^3$ | $R^1$  $R^2$ or $-N\diagdown\underset{R^2}{\overset{R^1}{}}$ | Physical data (m.p. = melting point) |
|---|---|---|---|
| 5 | $CH_3$  $CH_3$ | (3-CF$_3$-phenyl) | $n_D^{20}$: 1.4980 |
| 6 | $CH_3$  $CH_3$ | (cyclohexenyl) | $n_D^{20}$: 1.4930 |
| 7 | $CH_3$ | (3-ethylpiperidin-1-yl) | $n_D^{20}$: 1.4895 |
| 8 | $CH_3$  $CH_3$ | $C_4H_9$ | $n_D^{20}$: 1.4750 |
| 9 | $CH_3$ | (hexamethyleneimino) | $n_D^{20}$: 1.4930 |
| 10 | $CH_3$  $CH_2CH\!=\!CH_2$ | $CH_2CH\!=\!CH_2$ | $n_D^{20}$: 1.4860 |
| 11 | $CH_3$  $CH(CH_3)_2$ | (3-Cl-phenyl) | $n_D^{20}$: 1.5289 |
| 12 | $CH_3$  $CH(CH_3)_2$ | (4-Cl-phenyl) | m.p.: 108° C. |
| 13 | $CH_3$  $C_3H_7$ | $C_3H_7$ | $n_D^{20}$: 1.4745 |
| 14 | $CH_3$  $CH_3$ | (2,6-dimethylphenyl) | m.p.: 96° C. |
| 15 | $CH_3$  $CH_3$ | $CH_2C\!\equiv\!CH$ | $n_D^{20}$: 1.4923 |

STARTING SUBSTANCES OF THE FORMULA (II)

EXAMPLE (II-1)

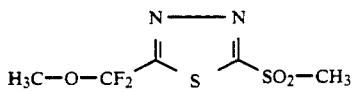

200 ml of 35% strength aqueous hydrogen peroxide solution are added dropwise to a stirred mixture of 40 g (0.16 mol) 5-methoxydifluoromethyl-2-methylthio-1,3,4-thiadiazole, 0.2 g of sodium tungstate and 140 ml of formic acid, which had been warmed to 50° C., during which process the temperature climbs to 95° C. for a short period. The reaction mixture is then cooled to 0° C., and the product which is obtained in the form of crystals is isolated by filtering off with suction.

22 g (56% of theory) of 5-methoxydifluoromethyl-2-methylsulphonyl-1,3,4-thiadiazole of melting point 45° C. are obtained.

STARTING SUBSTANCES OF THE FORMULA (IV)

EXAMPLE (IV-1)

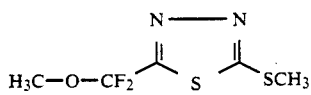

A solution of 61 g (1.13 mol) of sodium methoxide in 500 ml of methanol is added dropwise to a stirred solution of 245 g (0.9 mol) of 5-chlorodifluoromethyl-2-methylthio-1,3,4-thiadiazole in 600 ml of methanol, which had been cooled to 0° C. to 5° C. The reaction mixture is stirred for 12 hours at 20° C., and then poured into 2 l of water and shaken with 2 l of toluene. The organic phase is separated off, dried using sodium sulphate and filtered. The filtrate is concentrated under a waterpump vacuum and the residue is distilled under high vacuum.

95 g (50% of theory) of 5-methoxy-difluoromethyl-2-methylthio-1,3,4-thiadiazole are obtained as a colorless oil of boiling point 68° C./0.01 mbar.

STARTING COMPOUND OF THE FORMULA (V)

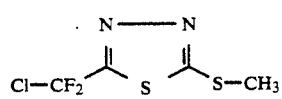

130 g (1.0 mol) of chlorodifluoroacetic acid are added dropwise at 20° C. to a solution of 69 g (0.5 mol) of potassium carbonate in 100 ml of water. After the addition of 1.5 l of toluene, the water is removed in a water separator. 121 g (1.0 mol) of methyl dithiocarbazate are added at approx. 25° C. to the remaining suspension with external cooling, and then 195 g (1.25 mol) of phosphorus oxychloride are added dropwise at 50° C. to 60° C. with this temperature being maintained. The reaction mixture is stirred for two hours and then poured into ice water, and the organic phase is separated off, washed with water, dried using sodium sulphate and filtered. The solvent is carefully removed from the filtrate by distillation under a waterpump vacuum.

190 g (88% of theory) of 5-chloro-difluoromethyl-2-methylthio-1,3,4-thiadiazole are obtained as an oily residue which can be purified by distillation under high vacuum. B.p.: 90° C.-95° C./1 mbar.

USE EXAMPLE

In the following Use Example, the compound of the formula below is used as comparison substance:

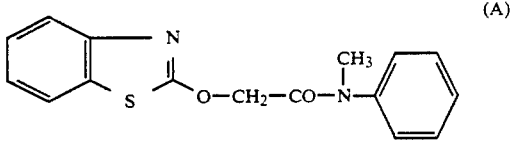

N-methyl-2-(benzothiazol-2-yl-oxy)-acetanilide (disclosed in U.S. Pat. No. 4,509,971).

EXAMPLE

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example the compounds according to Preparation Examples (1), (3), (4), (5), (6), (7), (9), (10), (11), (13) and (14) show a clearly superior activity compared with the prior art.

It is understood that the specification and examples are illustrative but not limitative of the present invention and that other embodiments within the spirit and scope of the invention will suggest themseleves to those skilled in the art.

What is claimed is:

1. A methylsulphonylthiadizaole of the formula

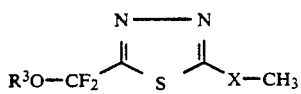

in which
R$^3$ stands for C$_1$-C$_6$-alkyl which is optionally substituted by halogen, C$_1$-C$_4$-alkoxy, C$_1$-C$_4$-alkylsulphonyl, phenyl, phenoxy or phenyl-C$_1$-C$_4$-alkoxy, the phenyl component being optionally substituted by halogen, C$_1$-C$_4$-alkyl, trifluoromethyl and/or C$_1$-C$_4$-alkoxy, and
X stands for S or SO$_2$.

* * * * *